(12) United States Patent
Marchitto et al.

(10) Patent No.: US 6,389,313 B1
(45) Date of Patent: May 14, 2002

(54) LASER PROBES FOR DRUG PERMEATION

(76) Inventors: Kevin S. Marchitto, 127 Bellbird Road; Stephen T. Flock, 17 Gillards Road, both of Mt. Eliza 3930 VIC (AU)

( * ) Notice: Subject to any disclaimer, the term of this patent is extended or adjusted under 35 U.S.C. 154(b) by 0 days.

(21) Appl. No.: 09/535,910

(22) Filed: Mar. 24, 2000

Related U.S. Application Data

(60) Provisional application No. 60/126,290, filed on Mar. 26, 1999.

(51) Int. Cl.[7] .................................................. A61N 1/30
(52) U.S. Cl. ........................................... 604/21; 607/92
(58) Field of Search ............................ 604/19–21, 113; 607/3, 88–94, 100–101, 104, 105, 120, 138; 600/101, 121, 127, 139, 153, 156

(56) References Cited

U.S. PATENT DOCUMENTS

| | | | | | |
|---|---|---|---|---|---|
| 4,175,545 | A | * | 11/1979 | Termanini | 128/666 |
| 4,641,912 | A | * | 2/1987 | Goldenberg | 350/96.01 |
| 5,151,096 | A | * | 9/1992 | Khoury | 606/15 |
| 5,246,437 | A | * | 9/1993 | Abela | 606/5 |
| 5,336,222 | A | * | 8/1994 | Durgin, Jr. et al. | 606/50 |
| 5,609,591 | A | * | 3/1997 | Daikuzono | 606/15 |
| 5,814,008 | A | * | 9/1998 | Chen et al. | 604/21 |
| 5,817,144 | A | * | 10/1998 | Gregory | 607/89 |
| 6,224,566 | B1 | * | 5/2001 | Loeb | 604/22 |

* cited by examiner

*Primary Examiner*—Sharon Kennedy
(74) *Attorney, Agent, or Firm*—Benjamin Aaron Adler

(57) ABSTRACT

The present invention provides an optical device/method for enhancing local administration of pharmaceutical compounds and/or collection of biomaterials. Such device/method is used for various situations which require high concentrations of drugs that are delivered locally.

28 Claims, 6 Drawing Sheets

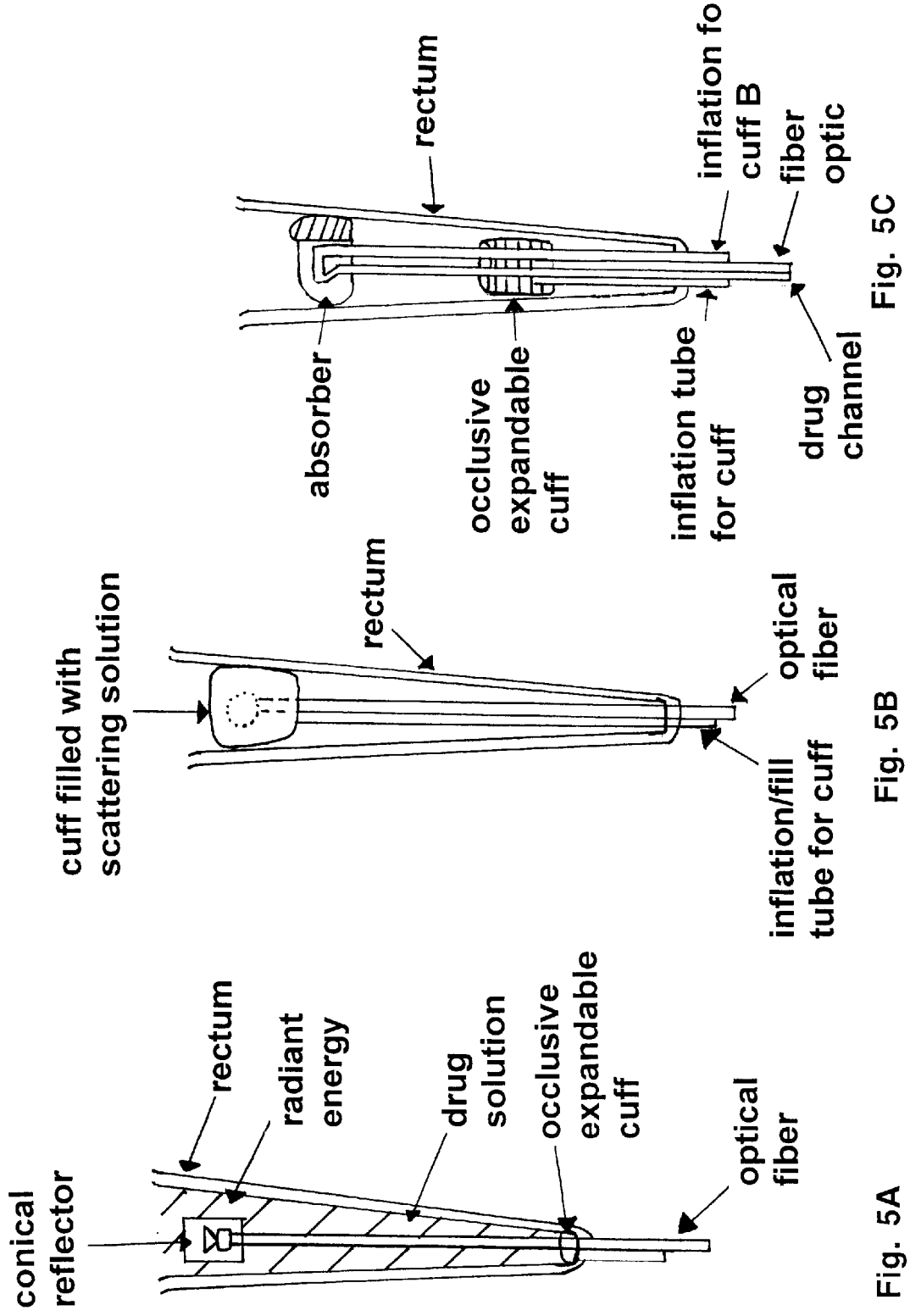

LASER PROBES FOR DRUG PERMEATION

CROSS-REFERENCE TO RELATED APPLICATION

This non-provisional patent application claims benefit of provisional patent application U.S. Ser. No.60/126,290, filed Mar. 26, 1999, now abandoned.

BACKGROUND OF THE INVENTION

FIELD OF THE INVENTION

The present invention relates generally to the fields of biomedical physics and drug delivery. More specifically, the present invention relates to laser probes for drug permeation for local administration.

DESCRIPTION OF THE RELATED ART

It is an axiom in pharmaceutical science that it is usually beneficial to maximize the local concentration of a biologically active material (pharmaceutic or biologic) in the tissue volume of interest. Similarly, it is typical that local administration is more desirable than systemic administration since the latter requires a higher dosage necessary for a therapeutic treatment, and often leads to an increase in side effects either systemically or at specific sites distal from the target tissue. However, local delivery of compounds is often not practical because the compounds do not significantly penetrate target tissues or tissues adjacent to or surrounding the site of interest.

Recently, multiple methods of making tissue more permeable to topically applied compounds were discovered. These methods can involve irradiating the tissue with the radiant energy produced by a laser before, during, or after drug administration. While these methods have been described elsewhere, the devices to make the methods feasible have not.

Chemotherapeutic drugs which exhibit a significant therapeutic effect are commonly used in cancer treatment. However, side effects and systemic dosage toxicity remain a problem in chronic treatment of disease. It is therefore beneficial to administer such drugs locally and in high concentrations for the more direct treatment of solid tumors. Local therapies are generally ineffective due to the difficulty to deliver the drugs to a local environment. Furthermore, tumor tissues are typically less vascularized, which results in poor drug uptake. Therefore, a means to enhance the tumor uptake of locally administered drugs, or even of drugs administered systemically, could result in increased efficacy and decreased systemic toxicity due to the lower dosage that is required.

Bone and joint infections include two disease processes known respectively as osteomyelitis and septic or infectious arthritis. As such, they are unique and separate infectious entities with different signs and symptoms caused by different infectious agents. Together these diseases affect more than 100,000 Americans annually. Introduction of oral antibiotic therapy has had a dramatic impact on these diseases. However, these diseases continue to cause a significant morbidity due to residual damage and chronic recurring infections.

The bone may be predisposed to infection through trauma such as a puncture wound or during surgery. However, infection may also reach the bone from adjoining soft tissue or from the bloodstream resulting in osteomyelitis. Infectious arthritis, on the other hand, is usually acquired from hematogenous spread. Chronic infection can persist for years. Patients with chronic osteomyelitis have a very poor prognosis. Dead bone and other necrotic material from the infection act as a bacterial reservoir and make the infection difficult to eliminate.

The patients are treated to eliminate the infection and prevent the development of chronic infection through high-dose intravenous antibiotics and/or surgical removal of dead bone tissue. Bone is a highly vascular mineralized connective tissue with internal trabeculae (where bone marrow and blood supply is situated) and a surrounding layer of solid cortical bone. Nevertheless, bone is less vascularized in advanced stages of disease, which makes it difficult to achieve high antibiotic concentrations. Therefore, methods and devices that improve the penetration of antibiotics in advanced stages of disease and deliver a high local concentration of antibiotic would be highly desirable.

Earaches in children are usually a result of otitis media, which commonly occurs when the eustachian (i.e. pharyngotympanic) tube (i.e., the narrow tube that connects the middle ear to the nasopharynx) becomes blocked. The blockage prevents fluid from draining out of the tube, which leads to bacterial or viral infection. More than 75% of children have at least one ear infection by their third birthday and almost 50% of children have had three or more infections before the age of three. Further, as the infection progresses, the bone may become involved resulting in significant permanent damage. A common complication of otitis in children is hearing loss. Recent studies indicate that up to 40% of children in the U.S. may have had some hearing loss due to infection. This hearing loss may be severe where infections are recurring or left untreated.

The treatment for earaches involves analgesics and oral antibiotics, a practice that is increasingly under scrutiny because of the related risks of developing resistance to antibiotics. In some cases, pressure-equalization (PE) tubes are inserted to drain fluids, pressure-equalization tubes, which are left in place for 6–9 months, perforate the tympanic membrane to allow fluid to drain. The placement of pressure-equalization tubes is done under general anesthesia, which has associated risks. The procedure itself may also lead to hearing defects. Topical administration of antibiotic to the tympanic membrane is impractical as the membrane is quite impermeable, and treatment of deep infection is limited due to large quantities required to be given orally. Thus, a means for delivering high local concentrations of drugs to the tympanic membrane would be useful for treating deep infections and preventing tissue damage.

Oral administration, the common route in drug administration, can sometimes be impractical. Other routes of administration might be more attractive under some pharmacokinetic issues. For example, rectal administration of drugs is potentially useful due to the rate and extent of rectal drug absorption. However, drug administration by this route can be problematic since the rectal mucosa is inherently not permeable. The most important clinical situation where rectal administration is desirable is in the case of pediatric or neonatal patients who cannot, or refuse to take oral medications. An effective means for delivering therapeutically active substances across the rectal mucosa would therefore be highly desirable for delivering a range of drugs to infants.

The prior art is deficient in the lack of effective means of enhancing local administration of pharmaceuticals and/or collection of biological materials. The present invention fulfills this long-standing need and desire in the art.

SUMMARY OF THE INVENTION

The present invention provides methods and devices for enhancing the local administration of pharmaceuticals or collection of biological materials from the body for therapeutic or diagnostic purposes. Pharmaceuticals or biological materials diffuse through membranes or anatomical structures which are not normally amenable to local drug administration or biomaterial collection.

The present invention further provides applications of the methods/devices in treating diseases such as solid cancers, bone infection and ear infection.

In one embodiment of the present invention, there is provided an optical device for enhancing delivery of a compound to or from a subject locally, comprising an optical probe with a tip; a source for radiant energy; a catheter for delivering the compound to or from the tip; a catheter for delivering radiant energy to the tip; and a means to observe placement of the tip. Optionally, the tip is further encased in a biocompatible sleeve. Alternatively, the tip is in contact with or be surrounded by a radiant energy absorbing material.

In another embodiment of the present invention, there is provided a method for enhancing delivery of a pharmaceutical compound to a subject locally, comprising the steps of irradiating the subject with radiant energy and administering a pharmaceutical compound to the subject, wherein both the radiant energy and pharmaceutical compound are delivered through the optical device disclosed above. Such method may be used for treating a solid tumor, a bone disease and an ear disease, or enhancing rectal administration of a pharmaceutical compound in an individual. For doing so, the optical device disclosed above is modified to fit each individual situation.

In still another embodiment of the present invention, there is provided a method for increasing diffusion rate of a substance in a medium, comprising the step of applying radiant energy to the medium, wherein the radiant energy generates propagating pressure wave upon the medium and is delivered through the optical device disclosed herein.

In yet another embodiment of the present invention, there is provided a method for improving permeation rate of a molecule through a barrier, comprising the step of applying radiant energy to the barrier, wherein the radiant energy is delivered through the optical device disclosed herein and ablates or alters the structure of the barrier.

In still yet another embodiment of the present invention, there is provided a method for creating pores in a barrier thereby improving permeation rate of a molecule through the barrier, comprising the step of applying radiant energy to the barrier, wherein the radiant energy is delivered through the optical device disclosed herein.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 5 shows a flexible endoscopic probe for rectal insertion. The probe carries channels for drug delivery and for optic assemblies. An optical absorber is shown in contact with the colon wall. An optional occlusive expandable cuff is also shown which prevents backflow of drugs during the delivery process. Alternative designs with conical reflectors and cuff with a scattering solution are shown. The probe provides radiant energy in a cylindrical pattern (FIG. 5A), isotropic geometry (FIG. 5B) or in a circular field created by deflecting the radiant energy laterally for more focal administration of drug (FIG. 5C).

DETAILED DESCRIPTION OF THE INVENTION

Figure 1:
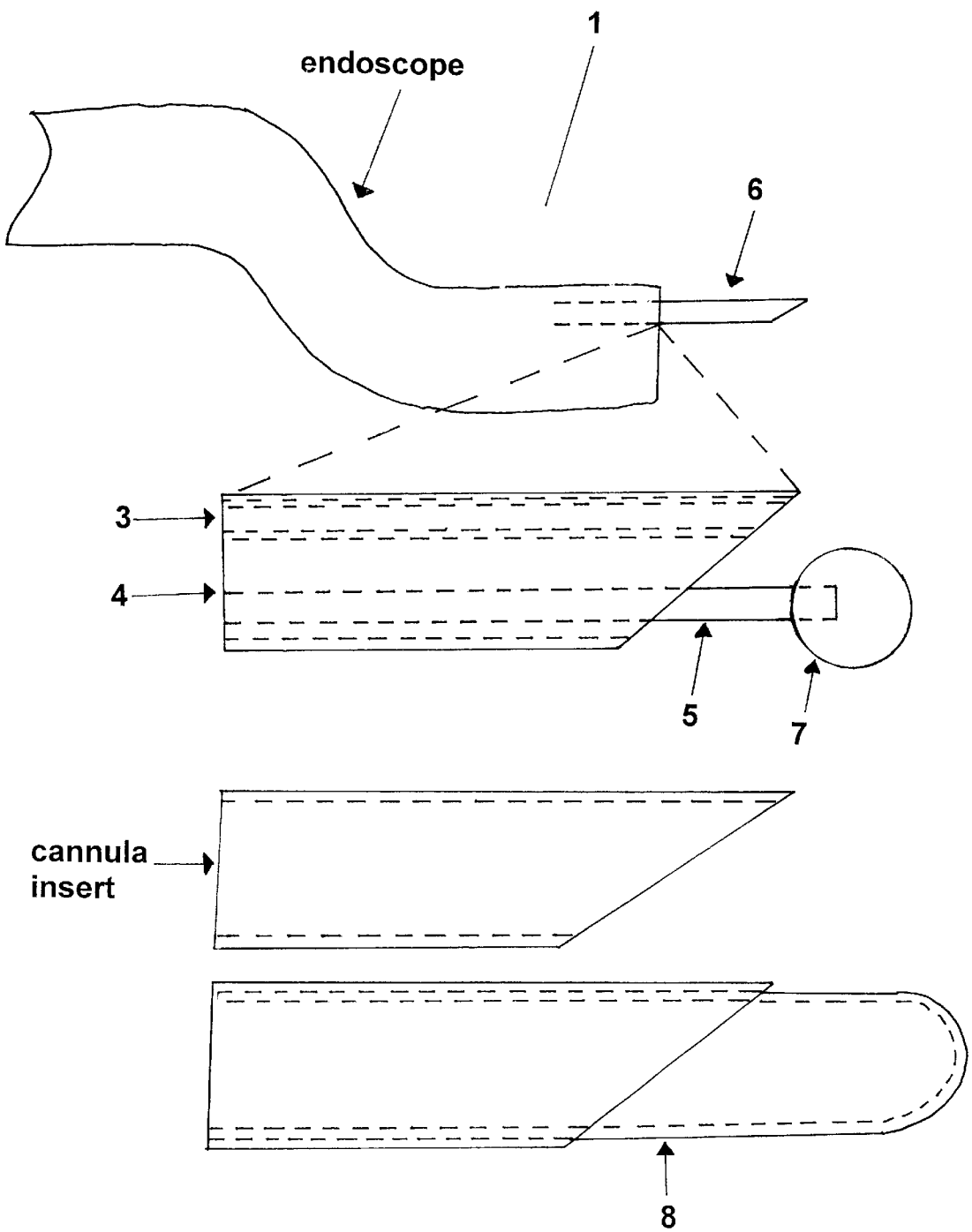
FIG. 1 shows an endoscopic device 1 which has a separate channel 3 for flow delivery of pharmaceutical substances, a channel 4 for light application, an optical fiber 5 carrying a probe 6 with a light diffusing tip 7, and optional external sleeve 8.

The present invention provides methods and devices for enhancing local administration of therapeutic or diagnostic materials to or from the body, through membranes as well as into or out of anatomical structures. Specifically, the present invention provides optical probes for use in treating solid cancers, bone infection, ear infection, colon or lower intestine disease, prostate disease, or administering drugs through epithelial or endothelial membranes.

In the present invention, radiant energy produced by laser is used to irradiate tissue of interest before, during, or after drug administration. Other electromagnetic energy, such as radiofrequency and microwave radiation, may also achieve similar results.

Non-ionizing electromagnetic energy (e.g. the infrared electromagnetic energy produced by an Er:YAG laser), delivered by catheters and related devices may be used to increase the diffusion rate of substances into or out of tissues. Such methods, referred to as delivery of "optical pressure", "optical pumping", or "optical propulsion" involve the creation of a type of pressure which serves to increase the rate of diffusion of substances through tissue interfaces. In one aspect, propagating pressure waves are used to create pressure in a medium such that the diffusion rate of the substances in the medium, usually a drug formulation, is increased relative to its surrounding environment.

In a related but distinctly different process, the pressure associated with propagating photons can also be applied directly to substances to push these substances through membranes or tissues. Such process is referred to as "optical propulsion." Optical propulsion relies on the delivery of photons that are absorbed or reflected off molecules, thereby exchanging momentum with a net force in the direction of the light. Alternatively, a "trap", such as an optical trap, is formed to create the pressure effect, which essentially "pulls" the molecules along a gradient. Finally, electromagnetic energy used to alter molecular structures in the mucosa or other tissue interface is discussed as a means of "opening" pores to further improve permeation rates.

In one embodiment of the present invention, there is provided an optical device for enhancing delivery of a compound to or from a subject locally, comprising an optical probe with a tip; a source for radiant energy; a catheter for delivering the compound to or from the tip; a catheter for delivering radiant energy to the tip; and a means to observe placement of the tip. Optionally, the tip is further encased in a biocompatible sleeve. Preferably, the tip scatters the radiant energy and is made of a radiant energy non-absorbing optical material. Alternatively, the tip is in contact with or be surrounded by a radiant energy absorbing material. Representative examples of radiant energy include laser, radiofrequency, light and microwave. Representative examples of pharmaceutical compounds include antibiotics, cytokines, bone vascularization enhancers, anesthetic drugs, antineoplastic drugs, photodynamic therapeutical drugs, anti-infection drugs, and anti-inflammatory drugs. Alternatively, the compound delivered can be a biomaterial desirous of removal from the subject. Still preferably, the catheter for delivering the compound and/or radiant energy is a flexible multi-lumen catheter. The placement of the tip can be monitored by an endoscope or a microscope.

In another embodiment of the present invention, there is provided a method for enhancing local delivery of a pharmaceutical compound to a subject, comprising the steps of irradiating the subject with radiant energy and administering a pharmaceutical compound to the subject, wherein both the radiant energy and pharmaceutical compound are delivered through the optical device disclosed above. Such a method may be used for treating a solid tumor, a bone disease and an ear disease, or enhancing rectal administration of a pharmaceutical compound in an individual. For doing so, the optical device disclosed above is modified to fit each individual situation. For example, the ear probe is placed in the external ear canal or passed up through the pharyngotympanic orifice into the middle ear. Specifically, the diseased bone suffers from osteomyelitis, septic arthritis, infectious arthritis, an infection caused by a wound or an infection caused by hematogenous spread, infiltration and adherence and the pharmaceutical compound used include antibiotics, cytokines, vascularization enhancers, anti-inflammatory drugs and other drugs that help to eliminate infection. In the case of rectal probe, the tip is placed against colon walls and the subject suffers from a pathologic state of colon, a pathologic state of lower intestine, or a pathologic state of prostate. The colon can be examined for polyps or cancerous lesions.

In still another embodiment of the present invention, there is provided a method for increasing diffusion rate of a substance in a medium, comprising the step of applying radiant energy to the medium, wherein the radiant energy generates propagating pressure wave upon the medium and is delivered through the optical device disclosed herein. Preferably, the medium is a solid or semi-solid medium.

In yet another embodiment of the present invention, there is provided a method for improving permeation rate of a molecule through a barrier, comprising the step of applying radiant energy to the barrier, wherein the radiant energy is delivered through the optical device disclosed herein and ablates or alters the structure of the barrier. Preferably, the barrier is a biological or non-biological barrier.

In still yet another embodiment of the present invention, there is provided a method for creating pores in a barrier thereby improving permeation rate of a molecule through the barrier, comprising the step of applying radiant energy to the barrier, wherein the radiant energy is delivered through the optical device disclosed herein.

The following examples are given for the purpose of illustrating various embodiments of the invention and are not meant to limit the present invention in any fashion.

EXAMPLE 1

Tumor Probe

A tumor probe is a radiant-energy waveguide device, which is made narrow enough for easy insertion into solid tumor masses, passing through anatomical passageways or through an endoscope to access a tissue of interest. The distal end of the probe is positioned into a tumor for local treatment and can be advanced into the tumor mass either through large vessels or through a perforation created by a cannula or similarly acting device.

The tip of the distal end of the probe (see probe 6 in FIG. 1) has an optical component which serves to scatter the radiant energy isotropically, more in the direction of a vector, or in a cylindrical pattern (FIG. 1). This tip 7 can be made up of a material that simply scatters but does not absorb the radiant energy, or of a non-absorbing/non-scattering optical material that directs separate beams in multiple directions. Alternatively, the scattering tip may be encased in an optically transparent biocompatible sleeve 8 (FIG. 1) to provide a gap between the tip and tissue of interest, thereby preventing adhesion of the tissue on the tip and excess treatment of the tissue adjacent to the tip. An optics assembly with a geodesic lens may provide appropriate directional scattering of the beam. The geodesic lens may have mirrored surfaces allowing the beam to be scattered internally prior to being emitted from the lens, providing equal opportunity for the beam to emerge from any single facet.

Figure 2:
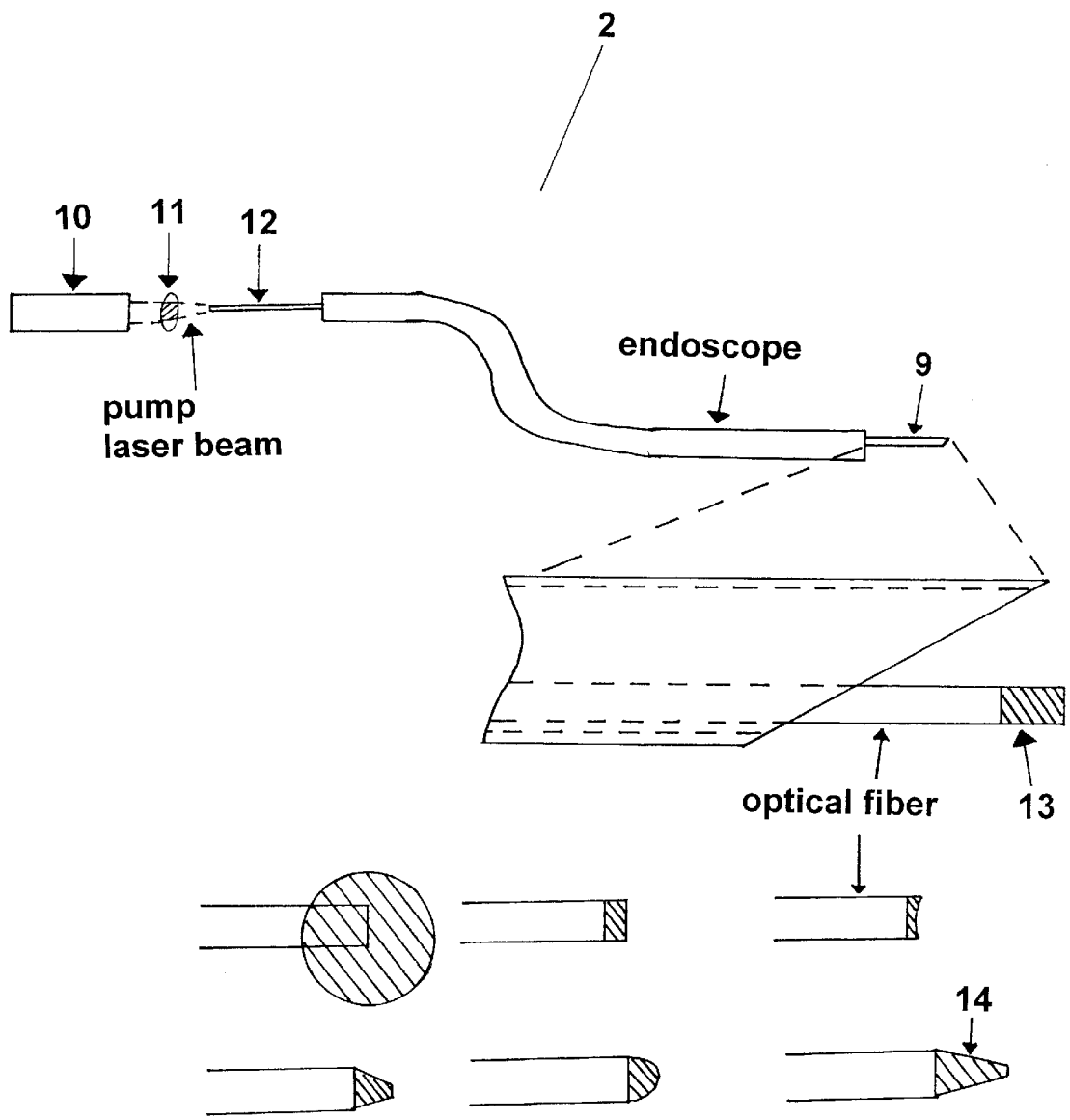
FIG. 2 shows an endoscopic probe 2 containing a fiber optic laser probe 9. The probe is coupled to a pump laser 10 with coupling optics 11 and optical fiber 12. A passively Q-switched microlaser 13 is optionally fitted at the distal end of the probe 9. Alternate styles of radiant energy absorbing tips 14 are shown. The radiant energy absorbing tip the same as the distal end of the probe.

Alternatively, the distal tip may be in contact with, or be surrounded by a material that serves to absorb the radiant energy (see radiant energy absorbing tips 14 in FIG. 2). Such absorbing material creates propagating pressure waves and is in intimate acoustic contact with the tissue, an acoustically conducting medium, or optionally a biocompatible sleeve (see in FIG. 1). The material can be of a particular shape so that when it vibrates, it directs pressure waves in a desired direction (see alternate styles of radiant energy absorbing tips 14 in FIG. 2).

Still alternatively, the endoscopic probe 2 may consist of a long, slender flexible multi-lumen catheter which carries elements to transmit energy to a diode-pumped solid-state microchip laser at the distal end (see passively Q-switched microlaser 13 for distal end of the probe in FIG. 2). The laser would be contained within a protective sleeve (see biocompatible external sleeve 8 in FIG. 1) eliminating the possibility of the tissue coming into direct contact with the laser. The radiant output of the laser would be either focussed into a direction beam for focal treatment of tissue in a forward direction or would be coupled into the scattering/non-absorbing tips. Use of an endoscope would allow one to simultaneously observe the placement of the tip, which serves to guide the electrical connections to the microchip pump laser 10 (see FIG. 2). Alternatively, the pump laser could be located extra corporeally (FIG. 2), and the radiant output of the pump could be guided to the solid-state microchip by means of an optical fiber passed down the catheter.

It would be beneficial if the endoscope has a channel for the pharmaceutically active substance or the biomaterial desirous of collection to pass through during the time that the probe is positioned within the tumor (see separate channel 3 in FIG. 1). The probe may be positioned with use of a flexible cannula under endoscope or radiological guidance. In this way the fiber optic (or the electrical connections) and drug channel cannula can be run transcutaneously where they are stabilized with bandage for the duration of the administration. Drugs are introduced through the drug channel at any time. The power supply and/or radiant energy source can be worn outside the body to render the patient ambulatory.

EXAMPLE 2

Osteomyelitis

Figure 3:
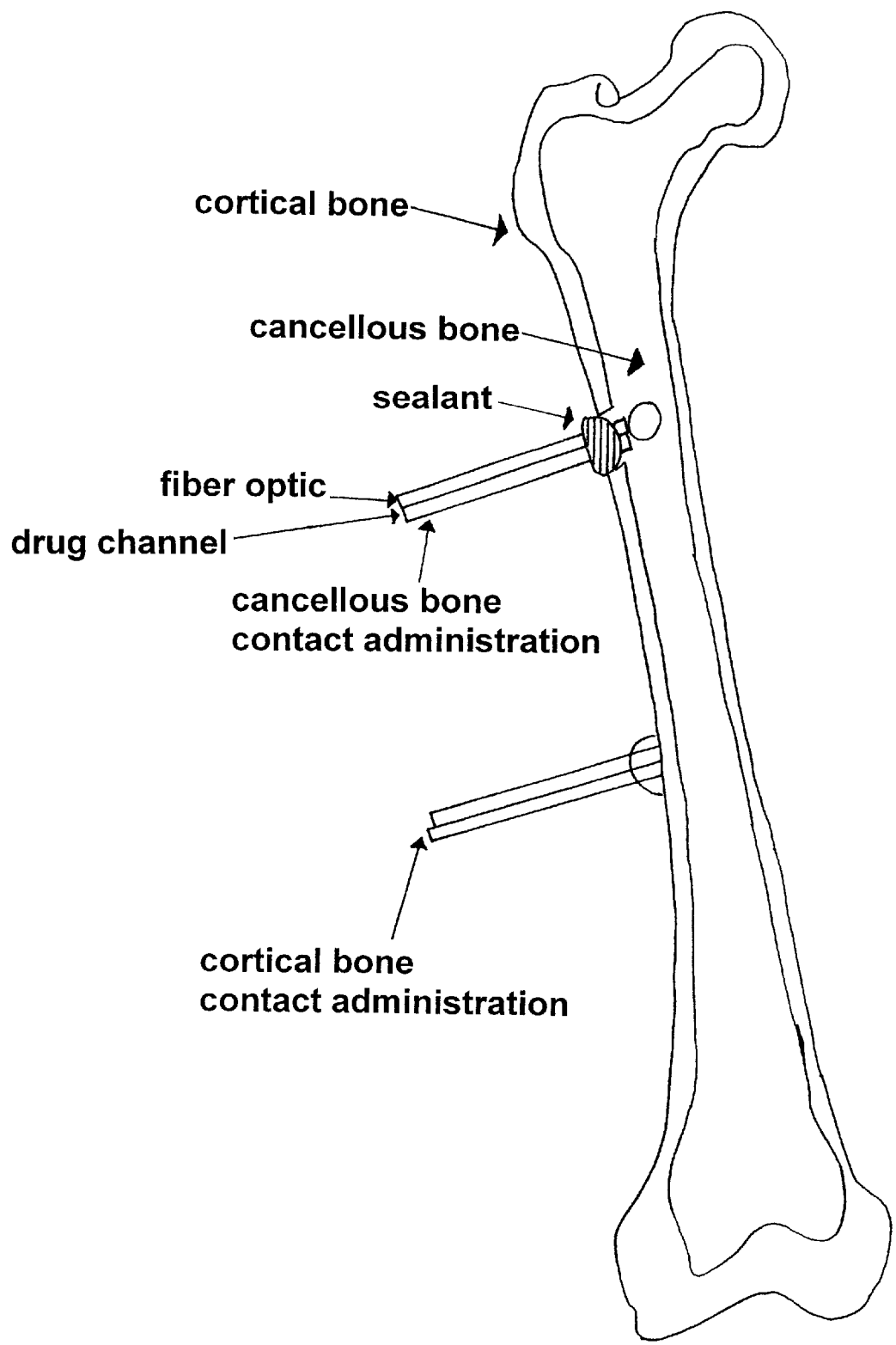
FIG. 3 shows the structure of a long bone to demonstrate devices for internal cancellous bone contact administration or external application to cortical bone. The probes carry drug channels and fiber optic assemblies.

The epiphyseal plate of the bone is extended through the external cortical layer into the trabeculae or cancellous bone (FIG. 3). Majority of the living cells associated with bones reside in cancellous bone. To maximize the delivery of antibiotic or other pharmaceutical substance to the cancellous bone in osteomyelitis, an optical probe may be placed adjacent to or within the lesion or site of infection and the radiant energy pumped into the lesion. Similar to the tumor catheter, the osteomyelitis catheter is introduced into the cancellous bone via an endoscopic device by first drilling a small hole through the cortical bone with a mechanical drill or laser. Alternatively, the endoscopic device itself may be fitted with a cutting tip that may or may not be retractable following insertion. Once the endoscope is in place, the catheter is advanced into the bone. A pack of biocompatible putty or sealant may be used to affix the catheter in place. As in the case of the tumor probe, the bone probe has a co-axial catheter suitable for administering the antibiotic and/or collecting biomatericals. The connections to the probe can be accessed transcutaneously and attached to power supplies, drug reservoirs, or radiant energy sources as described in the tumor probe.

The bone probes may be used to deliver antibiotics, cytokines (e.g. bone morphogenetic proteins which enhance bone regrowth), vascularization enhancers or other substances which help elimination of infection, healing, bone regrowth and vasculariazation. Such bone probes optically pump substances into the bone or even into cells. Drugs may be pumped deep into tissues in high local concentrations that were previously unachievable.

EXAMPLE 3

Ear Probe

Figure 4A:
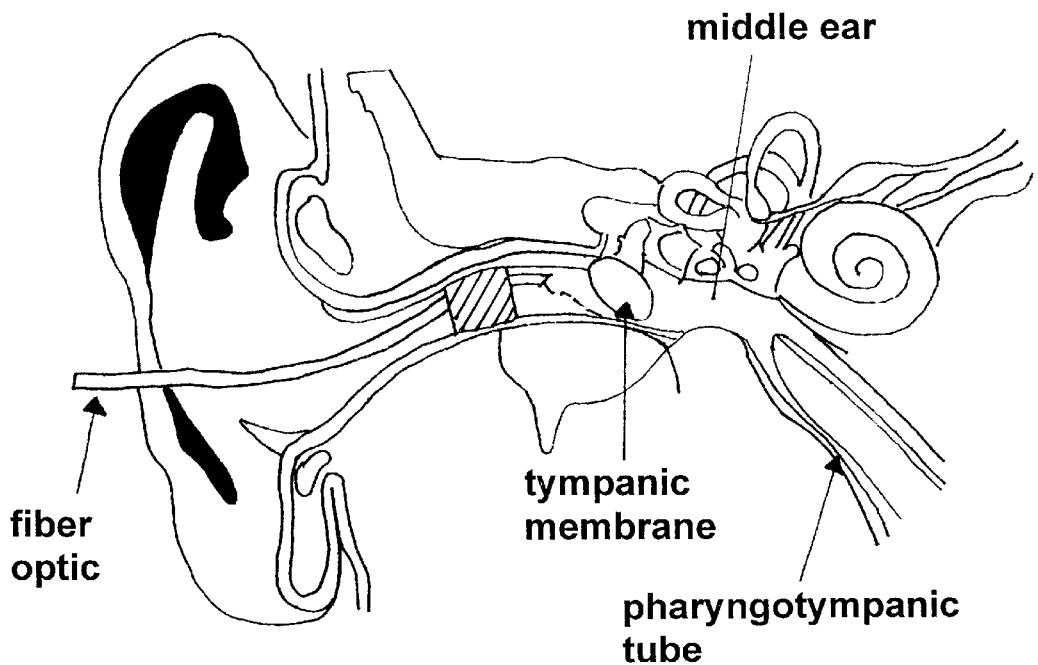
FIG. 4 shows the structure of a ear to demonstrate fiber optic delivery device with or without an occlusive seal to prevent backflow of pharmaceuticals. One design allows insertion through the pharyngotympanic orifice (FIG. 4B) while the other accesses the ear through the external ear canal (FIG. 4A).
Figure 4B:
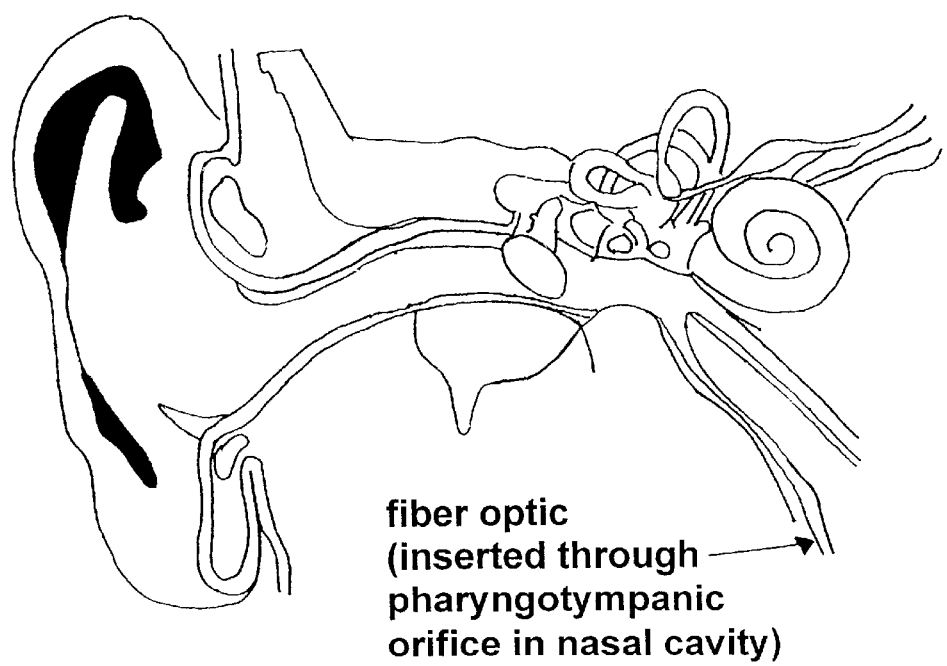

Ear probe is affixed in an occluding earplug. The earplug is made of a compressible material which expands when placed in the external ear canal and holds the probe in place (FIG. 4A). The output of the probe is directional in that the tympanic membrane or eardrum is irradiated. This irradiation directly forces pharmaceutically active substances into the tympanic membrane and/or beyond, depending on the energy and wavelength selected. The foam in the external ear canal can optionally be waterproof so that it holds the pharmaceutical in place between the earplug and the tympanic membrane. The connections to the probe can be run out of the external ear canal and attached to a mobile source of energy, drug and/or radiant energy. In doing so, the patient benefits from being ambulatory. Alternatively, an ear probe may be designed in such a way that the probe is passed up through the pharyngotympanic orifice into the middle ear (FIG. 4B). Such a probe may be used to deliver drugs through a narrow gauge catheter and deliver radiant energy through a small fiber optic (FIG. 4).

EXAMPLE 4

Rectal Probe

Rectal probe is fixed in a smooth sleeve of appropriate shape so that it can be inserted through the anal sphincter into the rectum (FIG. 5). The probe can be held in place by the anal sphincter and the tightness of the rectum, or by an expandable inflation cuff. The probe provides radiant energy in a cylindrical pattern (FIG. 5A), isotropic geometry (FIG. 5B) or in a circular field created by deflecting the radiant energy laterally for more focal administration of drug (FIG. 5C). Alternatively, the probe is held in place through an arrangement of inflatable balloons arranged coaxial with the fiber optic and drug channel.

Figure 5D:
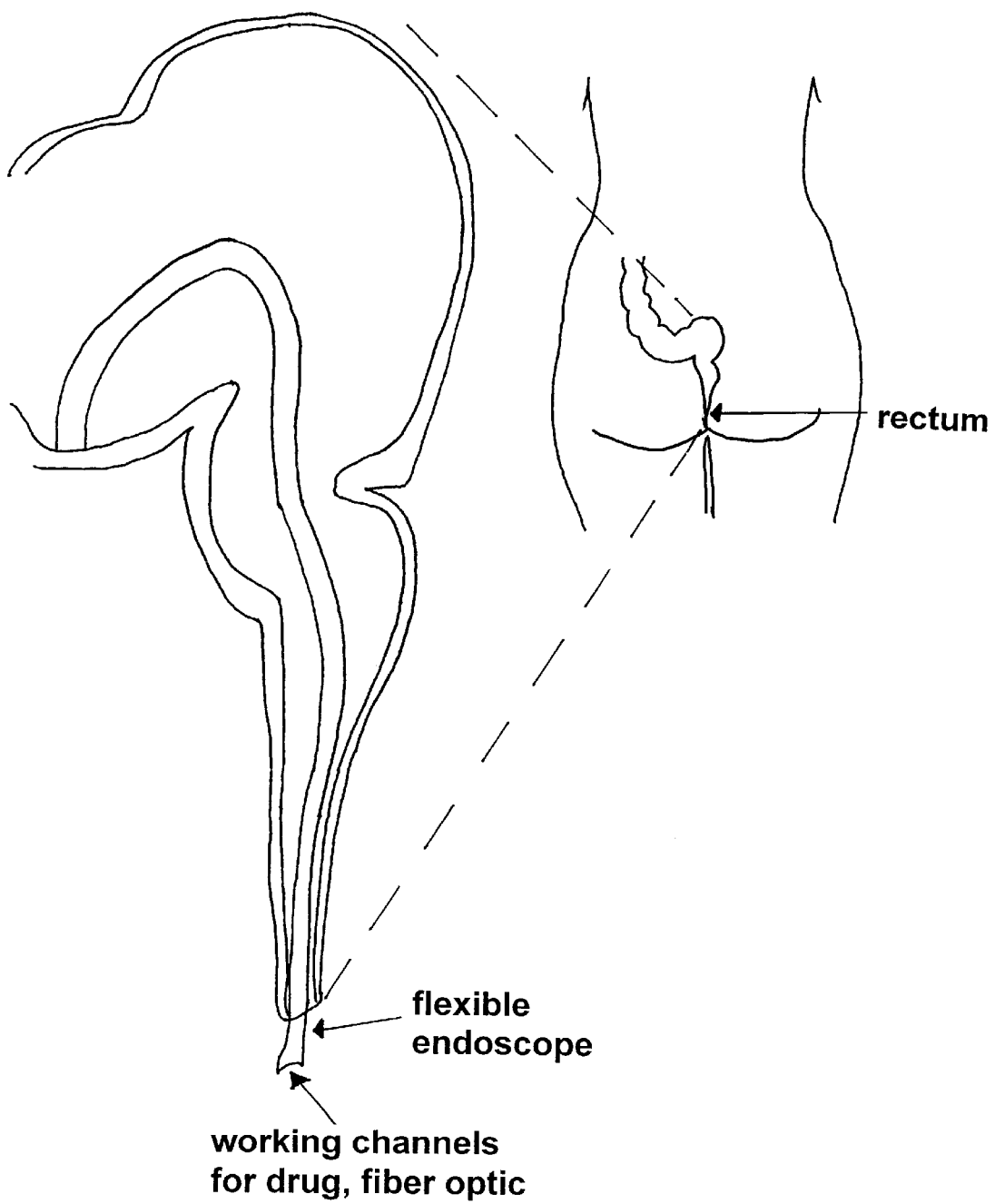
FIG. 5D demonstrates rectal insertion of the endoscopic probe.

Treatment can extend beyond the rectum into the colon or lower intestine. The probe may be encased in an endoscope, or the endoscope, probe and drug delivery channel encased in a catheter type device. The endoscope allows visual inspection of the colon walls for identification of polyps and/or cancerous lesions. These lesions may further be treated through direct contact with the rectal probe (FIG. 5D).

The rectal probe also provides a means to administer drugs to the prostate transmucosally. In this case, the probe is positioned against the rectum wall directly adjacent to the prostate. The radiant output of the probe is focal such that only the part of the mucosa in close proximity with the prostate is irradiated.

EXAMPLE 5

Pressure Wave Optical Pressure

Pressure waves created through the interaction of electromagnetic energy with tissue or non-biological matter may be used to drive molecules in a medium across tissue interfaces or between cellular junctions such as those found in membranes, between cells, or even through cellular membranes. For example, the interaction of laser irradiation with tissue can lead to the generation of propagating pressure waves (generated from a rapid volumetric change in the medium by heating, or by the generation of plasma) which are in the form of low pressure acoustic waves propagating at the speed of sound or high pressure shock waves propagating at supersonic speeds. These waves can also be a consequence of a generation of waves in a non-biological target that is in intimate acoustic contact with the biological media. These pressure waves may be applied to a pharmaceutical formulation in contact with the tissue to drive the substances in the formulation into the tissues. Continuously pulsing electromagnetic energy delivered in discrete short duration pulses propagates the pressure waves, which thereby creates a pressure that physically forces the substances in the formulation between cellular junctions or across membranes. The "pumping" effect may occur through the creation of increased pressure, including osmotic or atmospheric pressure. A separation results in a mobile phase due to the differential resistance of the tissues or membranes relative to the fluid medium.

EXAMPLE 6

Optical Propulsion

The aforementioned "pumping" effect may occur through the creation of increased pressure, including osmotic or atmospheric pressure. Continuous or pulsatile pressure may be applied directly to particles and molecules in a medium. In this aspect, the particulate or molecular object target would have different absorption or scatter characteristics than the medium such that the absorption or scatter of electromagnetic energy of the target results in an exchange of momentum from the photons to the target. As a result, the target is propelled at a differential rate relative to the medium. The ability of electromagnetic energy to push molecules through a medium is referred to as "optical propulsion." Optimally, the selected wavelength would neither result in a molecular nor electronic rearrangement as these two events would lead to the inefficient use of energy.

Light can exert forces on a molecule because photons carry momentum. The exchange of photon momentum with a molecule can occur incoherently, as in the absorption and readmission of photons, or coherently, as in the redistribution of (or lensing) of the incident field by the molecule.

EXAMPLE 7

Incoherent Force

The incoherent interaction that can alter the momentum of an atom is also called the "scattering force" because it arises from direct scattering events. Every time an atom scatters a photon carrying momentum $p=h/\lambda$ (h is Planck's constant and $\lambda$ is the wavelength of light), the atom experiences a small change in velocity. In the case of incoherent scattering, two momentum impulses are delivered to the atom: one along the direction of the incident photon and the other opposite the direction of the scattered photon. Because the photons in rare media are not scattered into a preferred direction, the net average velocity change per scattered photon $\Delta v$ is opposite the direction of the incident photons with $\Delta v = p/M = h/\lambda M$, where M is the mass of the atom. Note that this force also provides a means to separate atomic or molecular species based on their mass, M.

The momentum imparted on the molecular target in an inelastic collision is equal to the ratio of the photon energy, U, divided by the speed of light, c. Given a critical amount of energy fluence (rate) in the electromagnetic energy continuous-wave beam or pulse, significant forces can be imparted on the molecular target, thereby inducing movement since force is equal to the time derivative of momentum.

This incoherent force could, for example, be used in the following way. The electromagnetic energy produced by a pulsed or continuous-wave Nd:YAG laser (1064 nm wavelength) could be used to irradiate a molecule (such as lidocaine-HCl) which does not significantly absorb energy having such wavelength. The molecule, if placed on the skin for example, would then scatter the electromagnetic energy in such a way that the net momentum imparted upon the molecule is in a direction away from the surface of the skin. Thus, the penetration of the drug into tissue would be enhanced as compared to passive diffusion.

EXAMPLE 8

Coherent Force

The force arising from a coherent interaction with light is also called the dipole force. The laser field polarizes the atom, and the polarized atom experiences a force in the gradient of an electromagnetic field. The strong electric field of a laser beam can be used to induce a dipole moment in a process called optical trapping. As long as the frequency of the laser field is below the natural resonances of the particle being trapped (e.g. below the atomic transition of an atom or the absorption band of a polystyrene sphere), the dipole moment is in phase with the driving electrical field. Because the energy, W, of the induced dipole, p, in the laser field, E, is given by W=−pE; the particle achieves a lower energy state by moving into the high-intensity focal spot of the laser beam. There have been numerous reports of optical traps being used to manipulate particles, or even cells. These traps are used to move these tiny particles around under a microscope objective. Optical tweezers have also been described whereby a focal spot of a single beam optical trap is moved with mirrors or lenses. It has also been shown that other forms of electromagnetic energy may be used to form such "traps."

In the present invention, a trap is formed at the tissue interface where a desired molecular target is to be moved in a particular direction. In the case of drug delivery, the desired direction is into the tissues. Thus, the focal point of the trap is moved along a vector that penetrates the tissue of interest, while a formulation containing the drug is applied to the surface of the tissue. In the case of an optical trap, the focal point of a single beam or multiple beam trap would then be moved progressively into the tissue, which could occur cyclically so as to ensure the maximum pumping effect. Besides optical traps, other types of traps, such as magnetic, radiofrequency or microwave traps would also be useful.

EXAMPLE 9

A Specific Example of Tumor Probe

In the case of the tumor probe, an endoscope (available from Olympus Inc.) has a hollow tube for drug delivery passed down one of the working channels. The tube is made from fine surgical tubing (available from Intramedic, Inc.). The proximal end of the tube is placed over a needle affixed on a syringe filled with the appropriate medicament. The distal end of the tube is placed in a cannula of approximately 14 gauge. A standard silicon optical fiber of 250 micron diameter (available from Edmund Scientific) is passed down another working channel of the endoscope and into the cannula adjacent to the drug tube. The distal end of the optical fiber terminates in a 2 cm long cylindrical scattering tip (available from Miravant Inc.). The fiber tip and drug tube are positioned within the cannula as the cannula is advanced into the solid tumor under endoscopic guidance. Once positioned, the cannula is slightly retracted leaving the fiber tip and drug tube in place. The proximal end of the optical fiber is terminated in an SMA connector, which can be attached to a laser output coupling optical arrangement (available from Thor Labs Inc.). The radiant energy coupled into the optical fiber is produced by a pulsed Nd:YAG laser (available from Spectra-Physics Lasers, Inc.). The pulse has a width of about 250 microseconds, wavelength of 1064 nm, repetition rate of about 20 Hz, and energy of about 10 mJ.

Solid state Nd:YAG Q-switched microchip lasers are available from Uniphase Inc. These lasers are passively Q-switched and small enough so that they can be optically bonded to the end of a silica optical fiber. The device can then be clad in a protective coating like epoxy or heat-shrink tubing. The microchip laser can be pumped by guiding the radiant energy of a pulsed (up to 10 kHz) diode laser (as available from SDL, Inc.). This microchip laser/optical fiber could then be passed through a foam earplug which serves to hold the device in the external ear canal. The output of the laser can be passed through a cylindrical lens which would allow formation of a roughly rectangular spot which could cover more, or all of the tympanic membrane.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An optical device employing radiant energy to enhance local delivery of a compound to or from a subject, said optical device comprising:
    an optical probe with a tip;
    a source for radiant energy;
    a catheter for delivering a compound to or from said tip;
    a catheter for delivering radiant energy to said tip; and
    a means to observe placement of said tip;
    wherein said optical device is designed to enhance delivery of a compound by a method selected from the group consisting of applying optical pressure to generate propagating pressure waves in a medium to increase diffusion of a compound through said medium; applying optical pressure to a compound to directly drive said compound through membranes and tissue by optical propulsion; creating an optical trap to drive diffusion of a compound; and, directly applying radiant energy to tissue to increase the permeability of said tissue to a compound.

2. The optical device of claim 1, further comprising a biocompatible sleeve to encase said tip.

3. The optical device of claim 1, wherein said tip scatters said radiant energy.

4. The optical device of claim 3, wherein said tip is made of a radiant energy non-absorbing optical material.

5. The optical device of claim 1, wherein said tip is in contact with or be surrounded by a radiant energy absorbing material.

6. The optical device of claim 1, wherein said radiant energy is selected from the group consisting of laser, radiofrequency, microwave and light.

7. The optical device of claim 1, further comprising a compound wherein said compound is a pharmaceutical compound selected from the group consisting of antibiotics, cytokines, bone vascularization enhancers, anesthetic drugs, antineoplastic drugs, photodynamic therapeutical drugs, anti-infection drugs, and anti-inflammatory drugs.

8. The optical device of claim 1, further comprising a trap reservoir for a compound wherein said compound is a biomaterial desirous of removal from said subject.

9. The optical device of claim 1, wherein said catheter for delivering said compound or radiant energy is a flexible multi-lumen catheter.

10. The optical device of claim 1, wherein said means to observe placement of the tip is selected from the group consisting of an endoscope and a microscope.

11. A method for enhancing delivery of a pharmaceutical compound to a subject locally, comprising the steps of:
    irradiating said subject with radiant energy delivered through the optical device of claim 1; and
    administering said pharmaceutical compound to said subject, wherein said pharmaceutical compound is delivered through the optical device of claim 1.

12. The method of claim 11, wherein said compound is administered to treat a solid tumor.

13. The method of claim 11, wherein said pharmaceutical compound is an anti-cancer drug.

14. A method for treating a bone disease, comprising the steps of:
    irradiating the diseased bone with radiant energy delivered through the optical device of claim 1; and
    administering a pharmaceutical compound to said bone, wherein said pharmaceutical compound is delivered through the optical device of claim 1.

15. The method of claim 14, wherein said method further comprising the step of:
    collecting dead done tissues from said diseased bone.

16. The method of claim 14, wherein said bone suffers from a pathologic state selected from the group consisting of osteomyelitis, septic arthritis, infectious arthritis, an infection caused by a wound, an infection caused by hematogenous spread, infiltration and adherence.

17. The method of claim 14, wherein said pharmaceutical compound is selected from the group consisting of antibiotics, cytokines, vascularization enhancers, anti-inflammatory drugs and anti-infectives.

18. A method for treating an ear disease, comprising the steps of:
    irradiating the diseased ear with radiant energy delivered through the optical device of claim 1; and
    administering a pharmaceutical compound to said ear, wherein said pharmaceutical compound is delivered through the optical device of claim 1.

19. The method of claim 18, wherein the optical probe is placed in the external ear canal or passed up through the pharyngotympanic orifice into the middle ear.

20. A method for enhancing rectal administration of a pharmaceutical compound in an individual in need of such treatment, comprising the steps of:
    irradiating the individual's rectum with radiant energy delivered through the optical device of claim 1; and
    administering said pharmaceutical compound to said rectum, wherein said pharmaceutical compound is delivered through the optical device of claim 1.

21. The method of claim 20, wherein the optical probe is placed against colon walls.

22. The method of claim 20, wherein said individual has a pathological colon, a pathologic lower intestine, or a pathologic prostate.

23. The method of claim 22, wherein said pathologic colon is polyps or cancerous lesions.

24. A method for increasing diffusion rate of a substance in a medium, comprising the step of:
    applying radiant energy to said medium, wherein said radiant energy generates propagating pressure wave upon said medium, and wherein said radiant energy is delivered through the optical device of claim 1.

25. The method of claim 24, wherein said medium is a solid or semi-solid medium.

26. A method for improving permeation rate of a molecule through a barrier, comprising the step of:
    applying radiant energy to said barrier, wherein said radiant energy is delivered through the optical device of claim 1, and wherein said radiant energy ablates or alters the structure of said barrier.

27. The method of claim 26, wherein said barrier is selected from the group consisting of biological and non-biological barrier.

28. A method for creating pores in a barrier thereby improving permeation rate of a molecule through said barrier, comprising the step of:
    applying radiant energy to said barrier, wherein said radiant energy is delivered through the optical device of claim 1.

* * * * *